US00PP18912P2

(12) United States Plant Patent
Verschoor

(10) Patent No.: US PP18,912 P2
(45) Date of Patent: Jun. 10, 2008

(54) ***VERONICA* PLANT NAMED 'TOTAL ECLIPSE'**

(50) Latin Name: ***Veronica* sp.**
Varietal Denomination: Total Eclipse

(75) Inventor: Jan Verschoor, Haarlem (NL)

(73) Assignee: Witteman & Co, Hillegom (NL)

( * ) Notice: Subject to any disclaimer, the term of this patent is extended or adjusted under 35 U.S.C. 154(b) by 0 days.

(21) Appl. No.: 11/705,473

(22) Filed: Feb. 12, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Annette H Para
(74) *Attorney, Agent, or Firm*—Jondle & Associates, P.C.

(57) ABSTRACT

A *Veronica* plant particularly distinguished by many flowering stems with extremely dark blue flowers, short plant habit, healthy foliage and good mildew resistance.

2 Drawing Sheets

Genus and species: *Veronica* sp.
Variety denomination: 'Total Eclipse'.

BACKGROUND OF THE NEW PLANT

The present invention comprises a new and distinct cultivar of *Veronica,* botanically known as *Veronica* sp., and hereinafter referred to by the cultivar name 'Total Eclipse'. The new cultivar was found in 2005 in Haarlem, The Netherlands as the result of open pollination between many *Veronica* cultivars in 2004.

The new cultivar was discovered in 2005 in Haarlem, The Netherlands and has been asexually reproduced repeatedly by vegetative cuttings in Haarlem, The Netherlands over a one year period. The present invention has been found to retain its distinctive characteristics through successive asexual propagations.

SUMMARY OF THE INVENTION

The following are the most outstanding and distinguishing characteristics of this new cultivar when grown under normal horticultural practices in Haarlem, The Netherlands.

1. Extremely dark blue flowers;
2. Good mildew resistance;
3. Healthy foliage;
4. Short plant habit; and
5. Very floriferous with many flowering stems;

DESCRIPTION OF PHOTOGRAPHS

This new *Veronica* plant is illustrated by the accompanying photographs which show blooms, buds, and foliage of the plant in full color; the colors shown are as true as can be reasonably obtained by conventional photographic procedures.

DESCRIPTION OF THE NEW CULTIVAR

Figure 1:
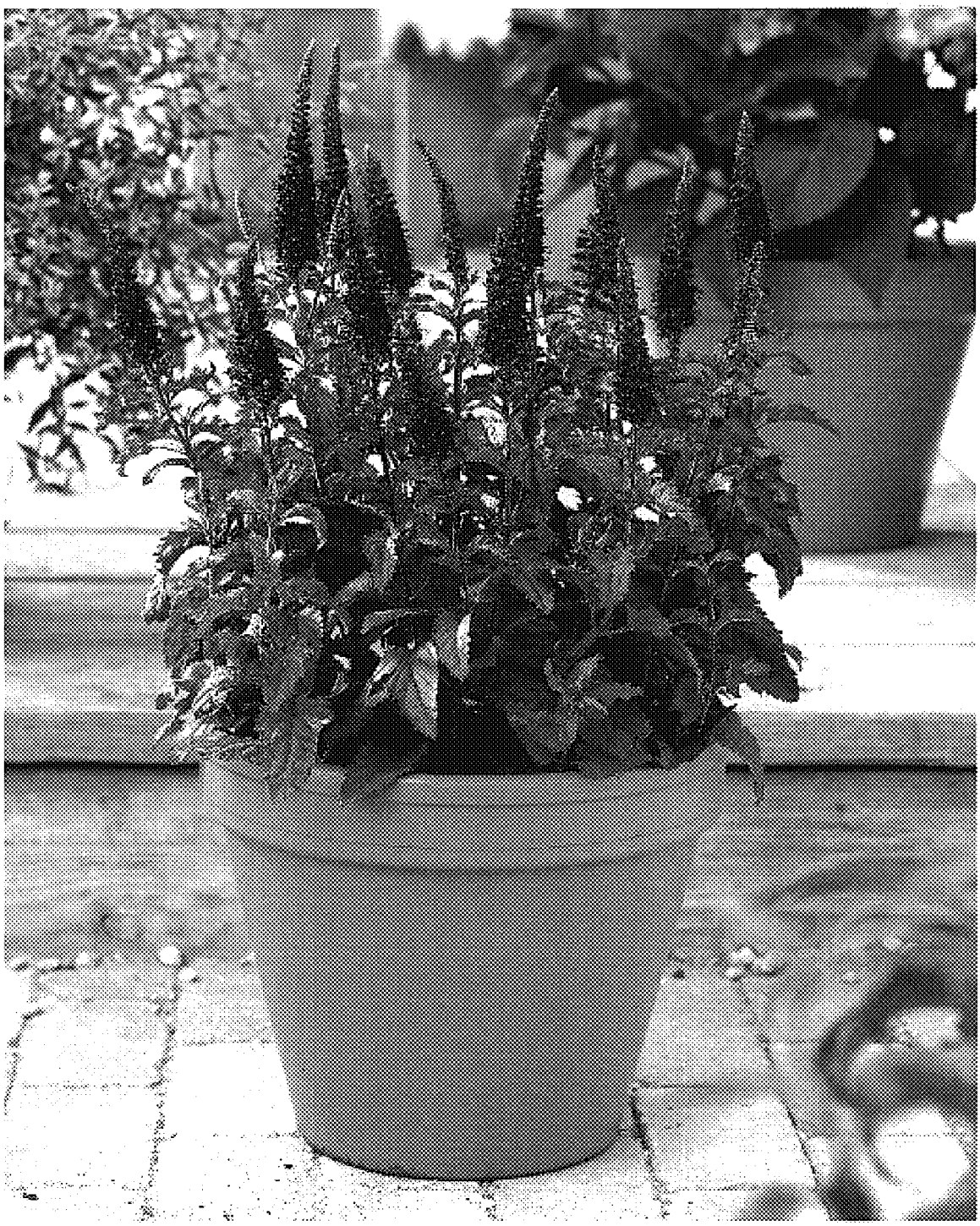
FIG. 1 shows the overall plant habit, including blooms, buds, mature foliage, and plant habit.
Figure 2:
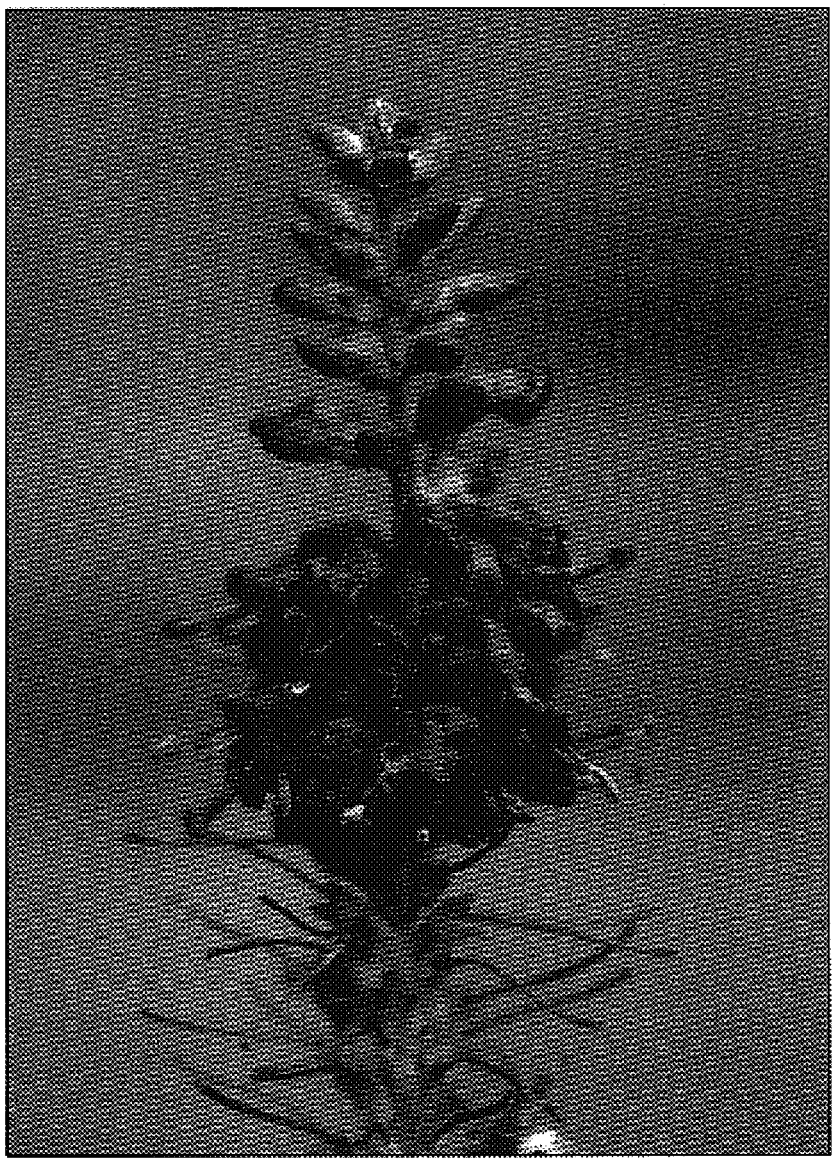
FIG. 2 shows a close-up of a mature inflorescence.
Figure 3:
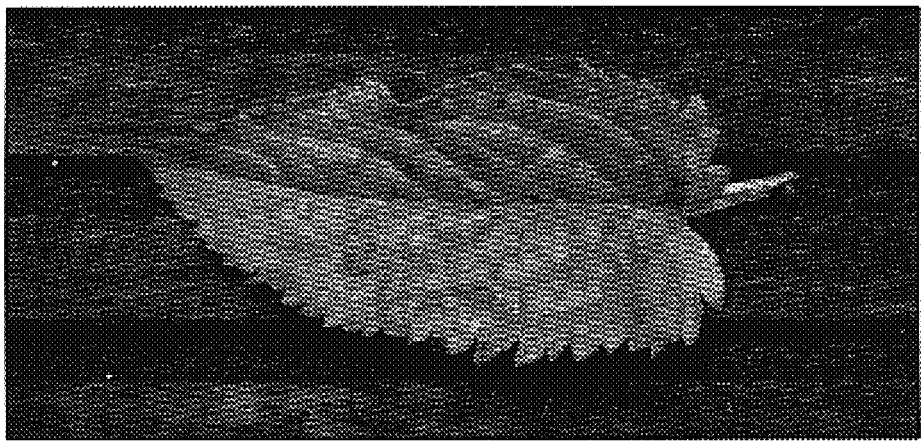
FIG. 3 shows a close-up of the mature leaf.

The following detailed descriptions set forth the distinctive characteristics of 'Total Eclipse'. The data which define these characteristics were collected from asexual reproductions carried out in Haarlem, The Netherlands. The plant history was taken on two-year-old plants field-grown in Haarlem, The Netherlands in September of 2006. Color readings were taken under natural light. Color references are primarily to The R.H.S. Colour Chart of The Royal Horticultural Society of London (R.H.S.) (2001 edition).

DETAILED BOTANICAL DESCRIPTION OF THE NEW PLANT

Classification:
- *Family.*—Scrophulariaceae.
- *Botanical.*—*Veronica.*
- *Common name.*—'Total Eclipse'.

Parentage:
- *Male parent.*—Unknown.
- *Female parent.*—Unknown.

Growth:
- *Plant habit.*—Upright.
- *Life cycle.*—Herbaceous Perennial.
- *Shape.*—Narrow inverted triangle.
- *Growth rate.*—In spring 10 cm per month.
- *Vigor.*—Moderate.
- *Flowering height* (*from top of soil*).—37.7 cm.
- *Width* (*horizontal plant diameter*).—22.9 cm.
- *Branching description.*—Freely branching.
- *Basal branching.*—Yes.
- *Lateral branches.*—Number: 5 stems. Length: 11.3 cm. Diameter: 0.25 cm. Internode length: 2.9 cm.
- *Time to produce a finished flowering plant.*—4 months.
- *Time to initiate and develop roots.*—About two weeks at 14° C.
- *Root description.*—Fine, grey.
- *How propagated.*—Vegetative cuttings.

Stem:
- *Appearance.*—Rounded, slightly glossy.
- *Strength.*—Strong.
- *Color.*—RHS 138A (Green).

*Pubescence.*—Densely pubescent; average length of hairs: 0.05 cm. Color: Light green-white.

Leaves:

*Durability of foliage to stress.*—High.

*Arrangement.*—Opposite, single.

*Quantity of leaves per lateral branch.*—14 (7 pairs).

*Immature leaf.*—Color: Upper surface: RHS 144A (Yellow-green). Lower surface: RHS 144C (Yellow-green).

*Mature leaf.*—Color: Upper surface: RHS 137A to RHS 137B (Green). Lower surface: RHS 138B (Green). Length: 5.9 cm. Width: 3.2 cm.

*Shape.*—Ovate.

*Apex.*—Acute.

*Base.*—Attenuate.

*Margin.*—Serrate (4.5 teeth per cm).

*Texture.*—Slightly glossy, slightly rugose.

*Venation.*—Pinnate.

*Venation color.*—Upper surface: RHS 145A (Yellow-green). Lower surface: RHS 145B (Yellow-green).

*Pubescence.*—Both sides are sparsely covered with short hairs. Length: 0.05 cm. Color: Light green.

*Petioles.*—Length: 1.2 cm. Diameter: Petiole is v-shaped, average width is 0.2 cm. Color: Upper surface: RHS 137A to RHS 137B. Lower surface: RHS 144B to RHS 144C. Texture: Smooth.

Inflorescence:

*Arrangement.*—Terminal Raceme.

*Flowering habit (length of flowering season).*—Continuously from July to late September.

*Lastingness of individual blooms.*—7 days.

*Number of inflorescences per plant.*—5.

*Quantity of flowers per lateral stem.*—125 per raceme.

*Quantity of flower buds per lateral stem.*—125 per raceme.

*Quantity of flowers and buds per plant.*—625.

*Time to flower.*—8 months when field-grown.

*Fragrance.*—None.

*Length.*—11.3 cm.

*Diameter.*—2.0 cm.

Inforescence buds:

*Length.*—0.4 cm.

*Diameter.*—0.2 cm.

*Shape.*—Obovate.

*Color.*—RHS N88B (Violet), underside of buds lighter: RHS N88C to RHS N88D; lower 30% of buds enclosed by calyx, immature calyx: RHS 143C (Green).

*Texture.*—Dull, smooth.

*Rate of opening.*—Approximately 20% opens at once, all flowers have opened in approx. 7 weeks; approximately 10% of flowers are opened at any stage.

Flowers:

*Aspect.*—Outward.

*Type.*—Campanulate.

*Flower length.*—0.9 cm.

*Flower diameter.*—0.5 cm.

*Persistant or self-cleaning.*—Persistant.

*Petals.*—Number: 4. Arrangement: Campanulate, lower 50% fused, upper 50% consisting of 4 lobes. Shape: Oblanceolate. Apex: Broadly acute. Base: Fused. Margin: Entire. Texture: Dull, smooth. Size: Length: 0.8 cm. Width: Average 0.2 cm, upper petal averages 0.35 cm. Color: Immature: Upper surface: RHS 90A (Violet-blue); lighter towards the base, RHS 90C to RHS 90D. Lower surface: RHS 90A (Violet-blue); lighter towards the base, RHS 90C to RHS 90D. Mature: Upper surface: RHS 90A (Violet-blue); lighter towards the base, RHS 90C to RHS 90D. Lower surface: RHS 90A (Violet-blue); lighter towards the base, RHS 90C to RHS 90D. Fading to: RHS N92B to RHS N92C (Violet-blue).

*Sepals.*—Arrangement: Rotate. Number: 4. Shape: Elliptic. Apex: Acute. Base: Cuneate, lower half fused. Margin: Entire. Texture: Dull, smooth. Color: Immature: Both surfaces: RHS 143C (Green). Mature: Both surfaces: RHS 143A to RHS 143B (Green). Size: Length: 0.2 cm. Width: 0.1 cm.

*Calyx.*—Shape: Rotate. Length: 0.2 cm. Diameter: 0.2 cm.

*Peduncle.*—Length: 11.3 cm. Diameter: 0.2 cm. Color: RHS 144A (Yellow-green). Angle: Straight upright (0°). Texture: Densely pubescent; average length of hairs: 0.05 cm. Strength: Strong.

*Pedicel.*—Length: 0.1 cm. Diameter: 0.05 cm. Angle: 50°. Strength: Strong. Color: RHS 144A to RHS 144B.

Reproductive organs:

*Stamens.*—Number: 2. Filament: Color: RHS 93A to RHS 93D at the base. Length: 0.6 cm. Diameter: 0.2 cm. Anthers: Shape: Dorsifixed, elliptic. Width: 0.1 cm. Color: RHS N92C (Violate-blue). Pollen amount: Sparse. Pollen color: RHS 162D (Greyed-yellow).

*Pistils.*—Number: 1. Pistil length: 0.8 cm. Stigma: Color: RHS N92B (Violet-blue). Shape: Clavate. Length: 0.1 cm. Diameter: 0.1 cm. Style: Color: RHS N92B (Violet-blue), base is RHS N88A to RHS N88B (Violet). Length: 0.7 cm. Diameter: 0.1 cm. Ovary: Shape: Short, ovate. Color: RHS 144C to RHS 144D (Yellow-green).

Fruit/seed set: No fruit or seeds produced.

Disease and insect resistance: No more susceptible or resistant than other *Veronica* varieties.

COMPARISON WITH COMMERCIAL CULTIVARS

'Total Eclipse' differs from the commercial cultivar 'Darwin's Blue' (U.S. Plant Pat. No. 13,070) in that 'Total Eclipse' has a darker blue flower, is a more compact, sturdier plant, with more mildew and rust resistance than 'Darwin's Blue'.

'Total Eclipse' differs from the commercial cultivar 'Purpleicious' (U.S. Plant Patent applied for) in that 'Total Eclipse' has a dark-blue flower while 'Purpleicious' has a purple flower. Additionally, 'Total Eclipse' is shorter with softer, rounder leaves of a lighter color, while 'Purpleicious' has sturdier, thicker, less rounded leaves, with a dark color.

I claim:

1. A new and distinct cultivar of *Veronica* plant as described and shown herein.

* * * * *